Feb. 16, 1965 D. L. ARMSTRONG Plant Pat. 2,474
ROSE PLANT
Filed Jan. 3, 1964
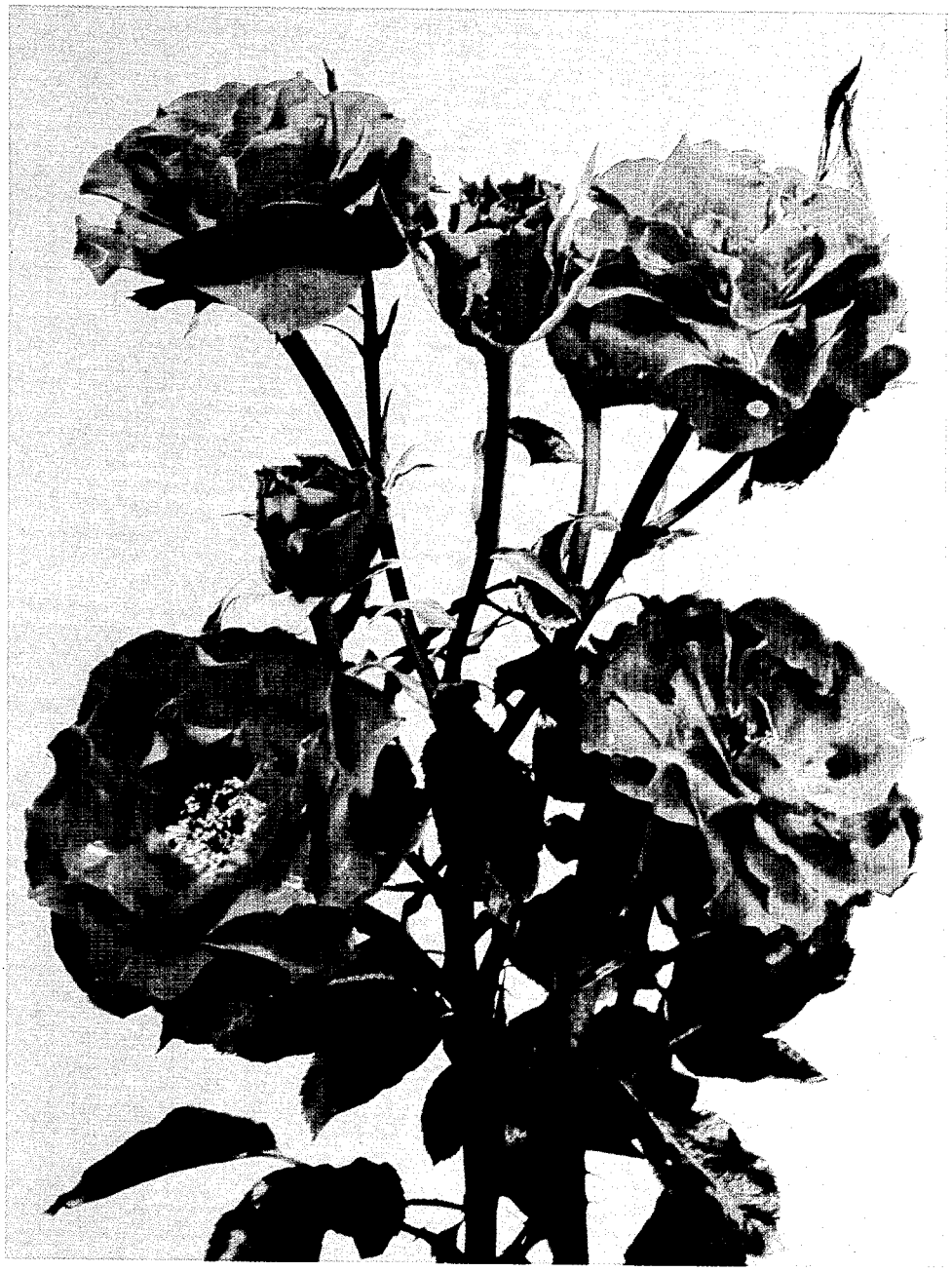
Inventor.
D. L. Armstrong
By: Robb & Robb
Attorneys.

United States Patent Office

Plant Pat. 2,474
Patented Feb. 16, 1965

2,474
ROSE PLANT

David L. Armstrong, Ontario, Calif., assignor to Armstrong Nurseries, Inc., Ontario, Calif., a corporation of California Filed Jan. 3, 1964, Ser. No. 335,704
1 Claim. (Cl. Plt.—20)

The present invention relates to a new and distinct variety of rose plant of a class falling midway between the hybrid tea and floribunda classes, said new variety having been originated by me by crossing the variety known as "Roundelay" (Plant Patent No. 1,280) with the variety known as "El Capitan" (Plant Patent No. 1,796), the former being the seed parent, and the latter being the pollen parent.

This new variety was selected as one of the outstanding results of an extensive breeding program conducted by me with the objective of producing improved rose varieties falling in a class between the hybrid tea and floribunda classes, with particular emphasis on doubleness of flour form, brightness of flower color in the red and orange-red color range, combined with good floriferousness. In the new variety which is the subject hereof, these objectives have been fully achieved, along with other desirable improvements, as evidenced by the following characteristics which are outstanding therein and which distinguish it from its parents, as well as from all other varieties of which I am aware:

(1) Vigorous, bushy, well branched and attractive plant habits;

(2) Glossy, disease-resistant foliage;

(3) Abundant flowers for its class, said flowers being borne both singly and in small clusters on stems of medium length and being evenly distributed over the plant;

(4) A quite double flower form and of medium size, with a combination of short flower petals and increasing tendency toward the center to stand upright and ruffle and fold inward, sometimes covering the center and giving an over-all attractive ruffled effect, reminiscent of carnation flowers;

(5) A distinctive, attractive and extremely bright and glowing orange-red flower color which particularly stands out and presents a striking contrast against the glossy green foliage; and (6) A very long flower life as compared with most rose flowers, which is attributable to the great substance of the individual flower petals.

In comparison with its seed parent "Roundelay," the new variety has only a slight suggestion of urn-shaped buds, with the open flowers being more cupped and the individual petals being rather short and tending to stand upright toward the center, contrary to the good urn-shaped bud form in the parent variety, with the open flowers of the latter having their petals laying back more; also, the orange-red color of the flowers of the new variety is distinctly different from that of the parent variety which is more red or dark red.

As compared with the pollen parent "El Capitan," the vigor of the new variety is somewhat less than that of this parent, which is extremely vigorous; the new variety has only a tendency toward urn-shaped buds, whereas the buds of this parent are nearly perfect urn-shaped; the flowers of the new variety are smaller and more double; the flower form is characterized by a tendency of the rather short petals to stand more vertically toward the center, with considerable ruffling of the inner petals, contrary to the considerably larger petals of the flowers of "El Capitan" in which the petals are less ruffled; and the flower color of the new variety is orange-red, which is distinctly different from the red flower color of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W) and Robert Ridgway's Color Standards and Nomenclature (hereinafter abbreviated (R), as indicated:

Type: Bush; outdoor; seedling; for cut flowers and for garden decoration.

Class: Between hybrid tea and floribunda classes.

Breeding: Seedling.

*Seed parent.*—"Roundelay."

*Pollen parent.*—"El Capitan."

Propagation: Holds its distinguishing characteristics through succeeding propagations by budding.

*Flower*

Locality where grown and observed: Ontario, California.

Flowers Borne: Sometimes singly, usually from 3 to 5 to a stem; in irregular clusters; on strong stems of medium length.

Quantity of bloom: Abundant, outdoors.

Continuity: Nearly continuous during growing season.

Fragrance: Slight.

Bud:

*Peduncle.*—Average length; average caliper; erect; stiff; usually smooth; with from few to several small gland-tipped cilia and few small prickles. Color—near Rainette Green, Plate XXXI (R), overlaid with near Buffy Olive, Plate XXX (R) on side exposed to the sun.

*Before calyx breaks.*—Size—from small to medium. Form—medium length; pointed.

*As calyx breaks.*—Color—between Current Red, Plate 821/1, page 167 (W) and Chrysanthemum Crimson, Plate 824/2, page 169 (W).

*Sepals.*—Inner surface—lined with fine, wolly tomentum. Outer surface—lined with several to many small stipitate glands. Alternate margins—lined with fine, wooly tomentum. Other margins—lined with from several to many small stipitate glands and sometimes with small, slender foliaceous parts.

*As first petal opens.*—Size—average. Form—medium length; from pointed to near urn-shaped. Color: outside—near Blood Red, Plate 820/1, page 166 (W), with small area at base of petal near attachment near Uranium Green, Plate 63/1, page 63 (W); inside—between Dutch Vermilion, Plate 717, page 156 (W) and Orient Red, Plate 819, page 165 (W), with small area at base of petal near Uranium Green, Plate 63/1, page 63 (W).

*Opening.*—Opens up well; is not retarded or prevented from opening by cold, hot, wet or dry weather.

Bloom:

*Size (when fully open).*—Average; from 3 inches to 3½ inches.

*Petalage.*—Double; from 45 to 55 petals, plus 2 to 6 petaloids; arranged irregularly.

*Form.*—High-centered at first, but becoming from cupped to high-centered; petals at first being tightly cupped, with tips slightly ruffled, but later becoming more loosely flat to cupped at maturity, with margins of outside petals usually reflexed downward; the quite double or tight grouping of the petals, their general shortness and their increasing tendency to stand upright toward the center and to have ruffled margins and to fold inward, often covering the center of the flower, gives an over-all ruffled effect or form reminiscent of the carnation flower.

Petals:

*Texture.*—Thick; leathery.

*Appearance.*—Inside—from satiny to velvety. Outside—satiny.

*Shape.*—Outside—between round and broadly obovate, with apex from flat to mucronate. Intermediate—from round to broadly obovate, with apex from flat to mucronate. Inside—between round and obovate, with apex usually rounded.

This description of a newly opened flower was made from a rose grown outdoors during the month of September at Ontario, California:

*Color.*—Outer petal: outside surface—between Currant Red, Plate 821/1, page 167 (W) and Cardinal Red, Plate 822, page 168 (W), with small area at base of petal near Uranium Green, Plate 63/1, page 63 (W); inside surface—between Dutch Vermilion, Plate 717, page 156 (W) and Orient Red, Plate 819, page 165 (W), with small area at base of petal near Uranium Green, Plate 63/1, page 63 (W). Intermediate petal: outside surface—between Blood Red, Plate 820/1, page 166 (W) and Currant Red, Plate 821/1, page 167 (W), with small area at base of petal near Uranium Green, Plate 63/2, page 63 (W); inside surface—between Dutch Vermilion, Plate 717, page 156 (W) and Orient Red, Plate 819, page 165 (W), with small area at base of petal near Uranium Green, Plate 63/2, page 63 (W). Inner petal: outside surface—between Blood Red, Plate 820/1, page 166 (W) and Currant Red, Plate 821/1, page 167 (W), with small area at base of petal near Uranium Green, Plate 63/3, page 63 (W); inside surface—between Dutch Vermilion, Plate 717, page 156 (W) and Orient Red, Plate 819, page 165 (W) with small area at base of petal near Uranium Green, Plate 63/3, page 63 (W).

This description was made from a rose that was open for three days outdoors during the month of September at Ontario, California:

*Color.*—Outer petal: outside surface—between Currant Red, Plate 821/1, page 167 (W) and Cardinal Red, Plate 822/1, page 168 (W), with small area at base of petal near Uranium Green, Plate 63/2, page 63 (W); inside surface—between Signal Red, Plate 719, page 93 (W) and Blood Red, Plate 820, page 166 (W). Inner petal: outside surface—between Blood Red, Plate 820/1, page 166 (W) and Currant Red, Plate 821/2, page 167 (W), with small area at base of petal near Uranium Green, Plate 63/2, page 63 (W); inside surface—between Signal Red, Plate 719, page 93 (W) and Orient Red, Plate 819/1, page 165 (W).

*General color effect.*—Newly opened flower—between Dutch Vermilion, Plate 717, page 156 (W) and Orient Red, Plate 819, page 165 (W). 3-days open—between Signal Red, Plate 719, page 93 (W) and Blood Red, Plate 820/1, page 166 (W).

*Behavior.*—Drop off cleanly; not particularly affected by cold, hot, wet or dry weather.

*Flower longevity.*—On bush in garden—5 days in September. Cut flowers grown outdoors and kept at living room temperatures—6 or 7 days in September.

*Reproductive Organs*

Stamens: Few; arranged regularly about pistils; a few mixed with petaloids.

Filaments: From short to medium length (from 3 mm. to 10 mm. long); most with anthers. Color—near Uranium Green, Plate 63/2, page 63 (W).

Anthers: From small to medium size; all open approximately at once. Color:—upper side—margins near Saffron Yellow, Plate 7/1, page 7 (W), with remainder near Empire Yellow, Plate 603/3, page 66 (W); under side—margins near Saffron Yellow, Plate 7/1, page 7 (W), with remainder near Empire Yellow, Plate 603/3, page 66 (W).

Pollen: From sparse to moderate abundance. Color—near Yellow Ochre, Plate 07, page 101 (W).

Pistils: Average number (approximately 75).

Styles: Moderately even; from short to average length (from 3 mm. to 12 mm. long); thin; bunched. Color—upper half of style near Indian Lake, Plate 826/2, page 170 (W), with remainder near Dresden Yellow, Plate 64/2, page 64 (W).

Stigma: Color—near Coral Pink, Plate 0619/3, page 182 (W).

Ovaries: Usually all enclosed in calyx.

Hips: Short; globular; smooth; walls thick and fleshy. Color (⅔ ripe)—near Courge Green, Plate XVII (R).

Sepals: Falling soon; medium length; straight. Color: inside—near Asphodel Green, Plate XLI (R); outside—near Kildare Green, Plate XXXI (R).

Seeds: Usually very few (from 1 to 10); from small to medium size.

*Plant*

Foliage:

*Leaves.*—Compound of usually 3 to 5 leaflets; abundant; from medium size to large; leathery; glossy.

*Leaflets.*—Shape—between oval and oblong. Apex—acute. Base—between round and acute. Margin—doubly serrate.

*Color.* — Mature. Upper surface — near Forest Green, Plate XVII (R); under surface—near Chromium Green, Plate XXXII (R). Young: upper surface—near Deep Dull Yellow-Green (1), Plate XXXII (R), with edges of leaflets overlaid with near Burnt Lake, Plate XII (R); under surface—near Apple Green, Plate XVII (R), overlaid with near Burnt Lake, Plate XII (R).

*Rachis (the supporting stem of the compound leaf).*—From light to average size. Upper side—grooved; with from few to several small stipitate glands on edges. Under side—smooth; with from none to few small stipitate glands and none to few small prickles.

*Stipules.*—Medium length; narrow; with short to medium length points turning out at an angle of more than 45°.

*Disease resistance.*—Better than average resistance to mildew, as determined by comparison with other varieties grown under comparable cultural conditions at Ontario, California.

Growth:

*Habit.*—Bushy; upright-spreading; much-branched.

*Growth.*—Free.

*Canes.*—Medium caliper.

*Main stems.*—Color—between Biscay Green, Plate XVII (R) and Light Elm Green, Plate XVII (R). Large prickles—from several to many; medium length; almost straight; with narrow base of medium length; color—near Pecan Brown, Plate XXVIII (R). Small prickles—from none to few; color—near Pecan Brown, Plate XXVIII (R). Hairs—none.

*Branches.*—Color—between Chromium Green, Plate XXXII (R) and Deep Dull Yellow-Green (1), Plate XXXII (R). Large prickles—from several to many; medium length; hooked slightly downward; with narrow base of medium length; color—near Hazel, Plate XIV (R). Small prickles—from none to few; color—near Hazel, Plate XIV (R). Hairs—none.

*New shoots.*—Color—near Apple Green, Plate XVII (R), overlaid with near Serpentine Green, Plate XVI (R) on side exposed to sun. Large prickles—from several to many; medium length; hooked slightly downward; with long, narrow base; color—near Deep Corinthian Red, Plate XXVII (R). Small prickles—from none to few; color—near Deep Corinthian Red, Plate XXVII (R). Hairs—none.

I claim:

A new and distinct variety of rose plant of the class falling between the hybrid tea and floribunda classes, substantially as herein shown and described, characterized particularly as to novelty by the unique combination of vigorous, bushy, well-branched and attractive habits of growth, glossy, disease-resistant foliage, abundant flowers borne both singly and in small clusters on stems of medium length, said flowers being evenly distributed over the plant and being of medium size and quite double in form, with short petals and increasing tendency thereof to stand upright toward the center and to ruffle and fold inward, sometimes covering the center and giving an over-all attractive ruffled effect reminiscent of carnation flowers, a distinctive, attractive, extremely bright and glowing orange-red flower color which strikingly contrasts with and stands out against the glossy green foliage, and a very long flower life attributable to the great substance of the individual flower petals.

No references cited.

ABRAHAM G. STONE, *Primary Examiner.*